(12) United States Patent
Moctezuma de la Barrera et al.

(10) Patent No.: US 8,457,719 B2
(45) Date of Patent: *Jun. 4, 2013

(54) FLEXIBLE TRACKING ARTICLE AND METHOD OF USING THE SAME

(75) Inventors: Jose Luis Moctezuma de la Barrera, Freiburg (DE); Donald W. Malackowski, Schoolcraft, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/963,394

(22) Filed: Dec. 8, 2010

(65) Prior Publication Data

US 2011/0077510 A1  Mar. 31, 2011

Related U.S. Application Data (63) Continuation of application No. 10/280,835, filed on Oct. 25, 2002, now Pat. No. 7,869,861.

(51) Int. Cl.
*A61B 5/00* (2006.01)
(52) U.S. Cl.
USPC ............... 600/426; 600/429; 606/130
(58) Field of Classification Search
USPC ... 606/130; 600/424, 426, 429, 407; 378/206, 378/164; 356/247, 248
See application file for complete search history.

(56) References Cited

U.S. PATENT DOCUMENTS

| | | | |
|---|---|---|---|
| 4,860,331 A | | 8/1989 | Williams et al. |
| 4,877,321 A | * | 10/1989 | Ichihashi et al. ............. 351/214 |
| 4,957,124 A | | 9/1990 | Mooney |
| 5,368,030 A | | 11/1994 | Zinreich et al. |
| 5,383,454 A | | 1/1995 | Bucholz |
| 5,430,509 A | * | 7/1995 | Kobayashi .................... 351/221 |
| 5,445,608 A | | 8/1995 | Chen et al. |
| 5,588,430 A | | 12/1996 | Bova et al. |
| 5,594,786 A | | 1/1997 | Chaco et al. |
| 5,676,673 A | | 10/1997 | Ferre et al. |
| RE35,816 E | | 6/1998 | Schulz |
| 5,765,561 A | | 6/1998 | Chen et al. |
| 5,769,861 A | | 6/1998 | Vilsmeier |
| 5,781,324 A | * | 7/1998 | Nishina ..................... 359/206.1 |
| 5,782,765 A | | 7/1998 | Jonkman |
| 5,813,984 A | | 9/1998 | Haaga et al. |
| 5,827,186 A | | 10/1998 | Chen et al. |
| 5,836,954 A | | 11/1998 | Heilbrun et al. |
| 5,873,822 A | | 2/1999 | Ferre et al. |
| 5,891,034 A | | 4/1999 | Bucholz |
| 5,954,647 A | | 9/1999 | Bova et al. |
| 5,967,980 A | | 10/1999 | Ferre et al. |
| 6,006,126 A | | 12/1999 | Cosman |
| 6,122,541 A | | 9/2000 | Cosman et al. |
| 6,127,672 A | | 10/2000 | Danisch |

(Continued)

*Primary Examiner* — Sanjay Cattungal
(74) *Attorney, Agent, or Firm* — Howard & Howard Attorneys PLLC (57) ABSTRACT

An article to enable the creation of a model of a surface includes a flexible substrate and multiple optical tracking points attached to the flexible substrate at predetermined location. The optical tracking points can be tracked by a tracking system, and a data link enables communication from the flexible substrate to a tracking system. Also disclosed is an article that enables the creation of a model of a surface including multiple light emitting diodes attached to the flexible substrate at predetermined locations. Finally, a method of registering an article and a method for creating a model of a surface having a shape are disclosed.

18 Claims, 6 Drawing Sheets

U.S. PATENT DOCUMENTS

| | | | |
|---|---|---|---|
| 6,149,643 A * | 11/2000 | Herekar et al. .................. 606/5 |
| 6,246,900 B1 | 6/2001 | Cosman et al. |
| 6,259,355 B1 | 7/2001 | Chaco et al. |
| 6,259,942 B1 | 7/2001 | Westermann et al. |
| 6,272,370 B1 | 8/2001 | Gillies et al. |
| 6,273,896 B1 | 8/2001 | Franck et al. |
| 6,275,725 B1 | 8/2001 | Cosman |
| 6,282,437 B1 | 8/2001 | Franck et al. |
| 6,298,262 B1 | 10/2001 | Franck et al. |
| 6,341,231 B1 | 1/2002 | Ferre et al. |
| 6,348,058 B1 | 2/2002 | Melkent et al. |
| 6,351,662 B1 | 2/2002 | Franck et al. |
| 6,402,762 B2 | 6/2002 | Hunter et al. |
| 6,445,943 B1 | 9/2002 | Ferre et al. |
| 6,491,699 B1 | 12/2002 | Henderson et al. |
| 6,529,765 B1 | 3/2003 | Franck et al. |
| 6,546,277 B1 | 4/2003 | Franck et al. |
| 6,561,648 B2 * | 5/2003 | Thomas ........................ 351/221 |
| 6,675,040 B1 | 1/2004 | Cosman |
| 6,697,664 B2 | 2/2004 | Kienzle, III et al. |
| 6,738,656 B1 | 5/2004 | Ferre et al. |
| 6,782,287 B2 | 8/2004 | Grzeszczuk et al. |
| 6,837,864 B1 | 1/2005 | Bertolero et al. |
| 6,926,673 B2 | 8/2005 | Roberts et al. |
| 7,117,027 B2 | 10/2006 | Zheng et al. |
| 7,200,251 B2 | 4/2007 | Joshi et al. |
| 7,483,049 B2 | 1/2009 | Aman et al. |
| 7,561,185 B2 * | 7/2009 | Yamasaki et al. ........ 348/208.99 |
| 2001/0016684 A1 | 8/2001 | Shahidi |
| 2001/0027271 A1 | 10/2001 | Franck et al. |
| 2001/0034530 A1 | 10/2001 | Malackowski et al. |
| 2002/0077543 A1 | 6/2002 | Grzeszczuk et al. |
| 2002/0087101 A1 | 7/2002 | Barrick et al. |
| 2002/0147455 A1 | 10/2002 | Carson |
| 2002/0188194 A1 | 12/2002 | Cosman |
| 2002/0198451 A1 | 12/2002 | Carson |
| 2003/0069591 A1 | 4/2003 | Carson et al. |
| 2003/0095186 A1 | 5/2003 | Aman et al. |
| 2003/0120283 A1 | 6/2003 | Stoianovici et al. |
| 2003/0130610 A1 | 7/2003 | Mager et al. |
| 2003/0159141 A1 | 8/2003 | Zacharias |
| 2004/0125361 A1 * | 7/2004 | Riza et al. ..................... 356/121 |
| 2006/0064030 A1 | 3/2006 | Cosentino et al. |
| 2006/0089626 A1 | 4/2006 | Vlegele et al. |
| 2009/0046152 A1 | 2/2009 | Aman |

* cited by examiner

FLEXIBLE TRACKING ARTICLE AND METHOD OF USING THE SAME

CROSS REFERENCE TO RELATED APPLICATIONS

This application is a continuation of U.S. patent application Ser. No. 10/280,835, filed Oct. 25, 2002, which is hereby incorporated by reference herein.

TECHNICAL FIELD

This invention relates to a flexible tracking article for use with a computer guided tracking system and a method of using the same. More particularly, this invention relates to a flexible tracking article for use with a computer guided surgical navigation system that can be registered with a preoperative or intraoperative scanned image with minimal patient discomfort.

BACKGROUND OF THE INVENTION

There are a wide variety of applications that require the identification and registration of a surface or shape with a previously created image. Certain manufacturing systems use the placement of tracking devices in predetermined locations to track the position of a work piece relative to an industrial process. Another use of this type of tracking system is in computer assisted or image guided surgical navigation systems.

The use of surgical navigation systems for complex surgical procedures has become relatively widespread. These surgical navigation systems use specially developed tools that include tracking devices so that the surgeon can see the position of the surgical tool overlaid on a monitor showing a preoperative or intraoperative image. The preoperative images are typically prepared using well-known preoperative scanning techniques, such as MRI or CT scans. The intraoperative images can be prepared using a fluoroscope, a low level x-ray, and similar devices. Tracking devices typically include multiple optical emitters such as LED's that can be detected by the surgical navigation system. The surgical navigation system can determine the position and/or orientation of the surgical tool from the position of the emitters.

In addition to tracking the surgical tool, the surgical navigation systems also must track or register the preoperative or intraoperative images to the patient in the operating arena so that the coordinate systems for the image files match the coordinate systems for the surgical navigation system. Typical registration procedures include placing fiducials or other markers at various locations on the anatomy of the patient. The preoperative or intraoperative scan is then performed with these markers in place and the markers then are either left in place until the surgery occurs or reapplied in the same position immediately prior to surgery. During the setup procedure before the surgical procedure, the scanned images in the computer are then registered to the patient by matching the location of these markers in the scanned images with the position of the actual markers on the patient in the surgical arena. Because the matching of the exact locations of these markers is critical to successful registration, the prior methods of attaching these markers usually involve an invasive procedure, such as attaching the markers themselves or a clamping device that carries the markers to bony areas of the patient. Alternatively, surgical personnel may use a permanent or semi-permanent marker to mark the patient at the locations where the markers or the clamping device are to be reapplied.

It is well recognized that the prior techniques are uncomfortable for the patient and often leave permanent marks or scarring. As a result, there have been numerous attempts to create less invasive markers for use in the registration of scanned images to the coordinate system of the surgical navigation system at the time of surgery.

In U.S. Pat. Nos. 6,122,541 and 6,248,900, a headband for frameless stereotatic registration is disclosed. This headband has markers, which can be visualized in the preoperative image scan and also includes LED's so that the headband can act both as a registration aid and as a tracking device for the patient during surgery. The system is registered during surgery by the standard registration practice of touching the tip of a tracking probe to each reference marker prior to beginning the surgical procedure.

U.S. Pat. No. 5,676,673 discloses a headset to be mounted on the patient. The headset is used to mount a reference unit such as magnetic field generator to track a surgical instrument inside the patient relative to the preoperative image. Registration of the image to the patient is accomplished using conventional fiducial type markers attached to the patient's skin.

SUMMARY OF THE INVENTION

According to one aspect of the present invention, a method of registering an article having a surface to previously created scan data of the article includes the steps of providing a flexible substrate having multiple tracking points attached to the substrate, applying the substrate to the article to be registered, creating a model of the surface of the article from a location of each tracking point, and registering the model with the previously created scan data.

According to a further aspect of the present invention a method of creating a model of a surface having a shape includes the steps of providing a flexible substrate having multiple tracking points attached to the substrate, attaching the flexible substrate to the surface, determining a location for each tracking point, and calculating the shape of the surface from the location of each tracking point.

According to an still further aspect of the present invention an article to enable the creation of a model of a surface includes a flexible substrate, multiple tracking points attached to the flexible substrate at predetermined locations, wherein the tracking points can be tracked by a tracking system, and a data link to enable communication from the flexible substrate to a tracking system.

According to a yet further aspect of the present invention an article to enable the creation of a model of a surface includes a flexible substrate, multiple light emitting diodes attached to the flexible substrate at predetermined locations, wherein each light emitting diode is in a fixed relation to its neighboring light emitting diodes; and a data link to enable communication from the flexible substrate to an optical tracking system.

Other aspects and advantages of the present invention will become apparent upon consideration of the following detailed description.

DETAILED DESCRIPTION OF THE PREFERRED EMBODIMENTS

Figure 1:
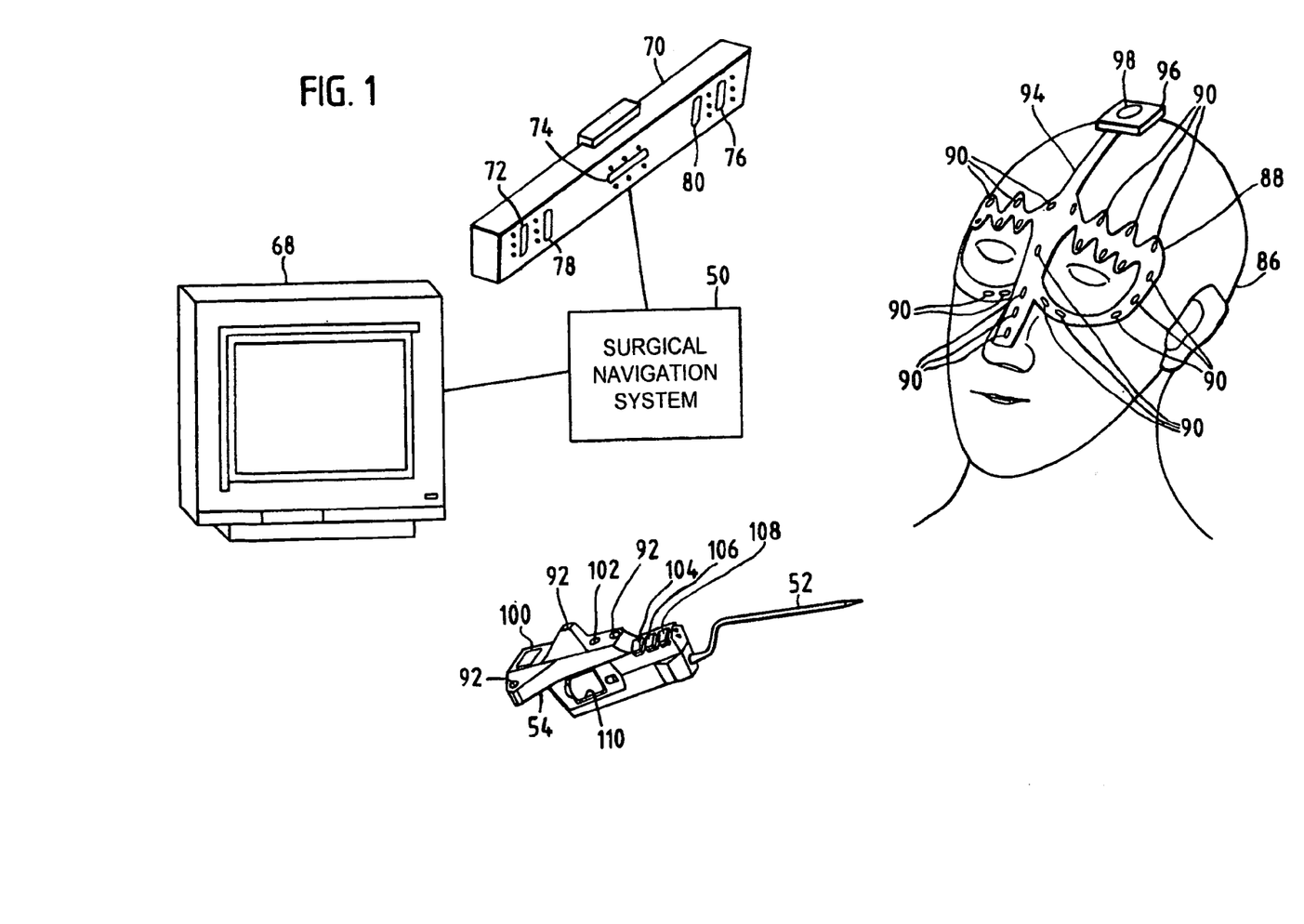
FIG. 1 is a schematic representation of the surgical navigation system using the flexible tracking device and method of the present invention.
Figure 2:
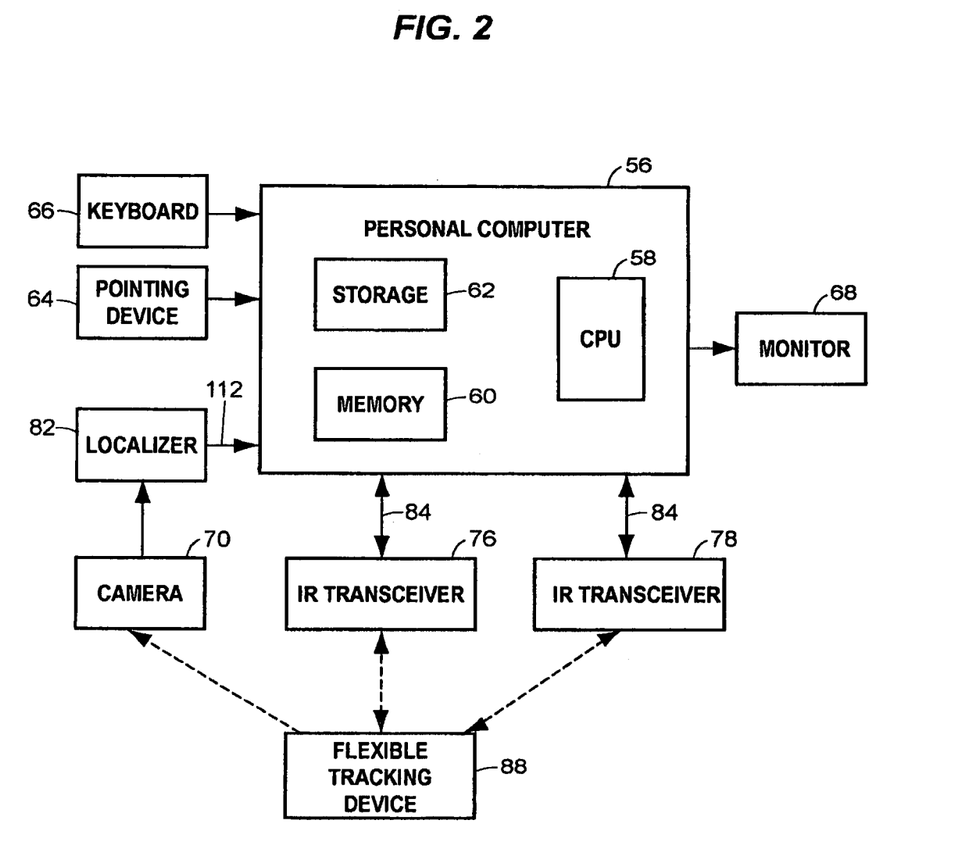
FIG. 2 is a block diagram of the surgical navigation system of FIG. 1.

FIGS. 1 and 2 are a schematic view and a block diagram of a surgical navigation system 50 adapted to track a surgical tool 52 having a tool tracking device 54 associated therewith. The surgical navigation system 50 includes a personal computer 56 that has an internal CPU 58, a memory 60 and a storage device 62. Also associated with the personal computer 56 are a pointing device or mouse 64, a keyboard 66 and a monitor 68.

The surgical navigation system 50 also includes a camera 70, which is comprised of three separate CCD camera arrays 72, 74 and 76. These camera arrays 72, 74 and 76 are adapted to detect infrared signals generated by the tool tracking device 54 and also by a flexible tracking device 88. The camera 70 can be conveniently mounted to a cart (not shown) or can be physically mounted or attached to an operating room wall (not shown) or to a operating room light (not shown). The surgical navigation system 50 also includes a localizer 82 that cooperates with the camera 70 to identify the location of LED's on the flexible tracking device 88 and LED's 90 on the tool tracking device 54, as well as any other tracking devices that may be within the field of the camera 70. The CCD camera arrays 72, 74 and 76 contain their own calibration information and transmit the position data from the various LED's to the localizer 82. The localizer 82 then converts the raw position data into position and orientation data using techniques well known to those of skill in the art. The localizer 82 communicates the position and orientation data to the personal computer 56 through a cable 112. The camera 70 also includes two infrared transceivers (IR) 78 and 80 that are capable of communicating with the flexible tracking device 88, the tool tracking device 54, and any other suitable tracking devices within the view of the camera 70. The transceivers 78 and 80 are directly connected to computer 56 through a separate circuit in a cable 84. The flexible tracking device 88 has an IR transceiver 98 built into a battery pack 96, which is attached to the flexible tracking device 88 by a cable 94. Similarly, the tool tracking device 54 has an IR transceiver 100 also capable of communicating with the IR transceivers 78 and 80. The tool tracking device 54 also includes a status light 102 and a plurality of buttons 104, 106 and 108 that are capable of being programmed to transmit certain signals through the IR transceiver 100 to the surgical navigation system 50. The tool tracking device 54 also includes a battery 110.

Figure 3:
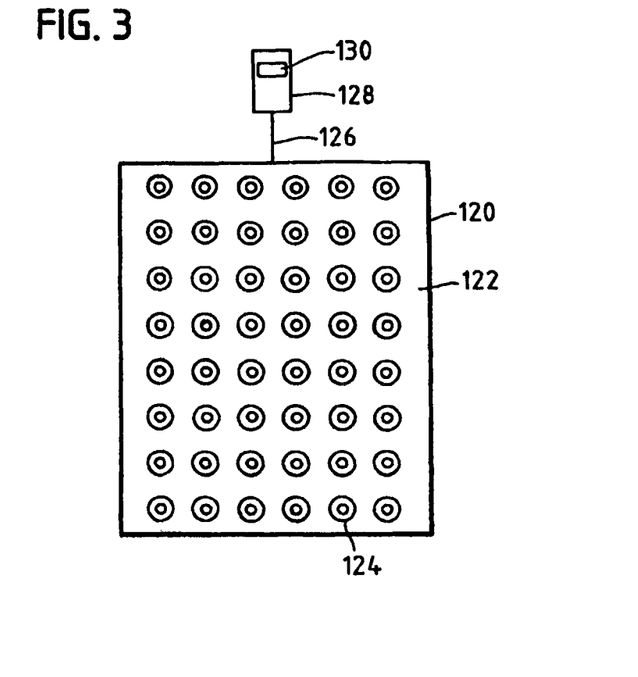
FIG. 3 is a plan view of one embodiment of the multiple tracking device of the present invention.

With regard to FIG. 3, a second embodiment 120 of the flexible tracking device of the present invention is shown. The flexible tracking device 120 includes a flexible sheet 122 having a 6×8 array of LED's 124 affixed to the surface thereof. As shown in FIG. 3, the 6×8 array of LED's 124 are all powered by a power source such as a battery pack 128 which is attached to flexible sheet 122 by cable 126. The battery pack 128 also includes an IR transceiver 130 similar to that discussed above. For simplicity, the wiring from the battery pack 128 to each of the LED's in the 6×8 array of LED's 124 is not shown, however each LED in the 6×8 array of LED's 124 is connected to the battery pack 128 and is capable of being independently illuminated so that surgical navigation system 50 can determine the position of each individual LED in the 6×8 array of LED's 124. The flexible sheet 122 has a layer of light adhesive on one side and is stuck on to the patient 86 using this adhesive. The LED's in the 6×8 array of LED's 124 that are visible to camera 70 can be used by the surgical navigation system 50 for surface matching as well as patient tracking.

The geometry of the sheet 122 can be initialized by tracking rigid tissues of the patient 86 after determining the spatial relationship of the 6×8 array of LED's 124 with the camera 70. A second mode of initialization is to track soft tissue displacement or deformation over time. Using the first mode, the positional information of the flexible sheet 122 and the 6×8 array of LED's 124 can be used to register the tracked feature of the patient to an image data set, such as a CT scan, using, for example, surface matching techniques.

Figure 4:
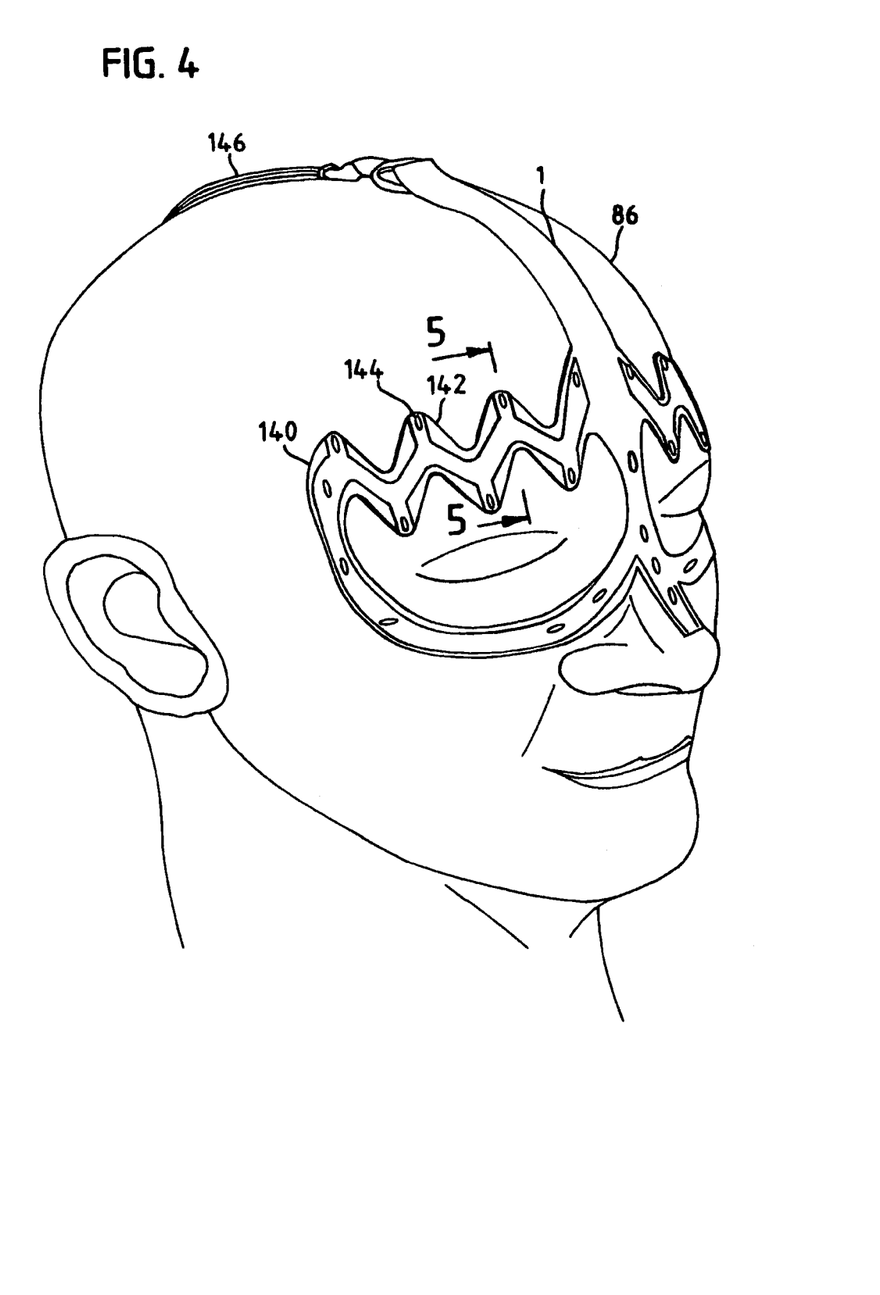
FIG. 4 is an isometric view showing a flexible tracking device of the present invention adapted for ear, nose and throat surgery affixed to a patient.

With reference to FIG. 4, a third embodiment of the flexible sheet of the present invention is shown. In this embodiment, a flexible tracking device 140 is similar to the flexible tracking device 88 and has a flexible sheet 142 having an array of LED's 144 spaced at known intervals from each other. The array of LED's 144 differs from the 6×8 array of LED's 124 in that it is not a rectangular array. Nonetheless, each LED 152 in the array of LED's 144 is in known relationship to its neighbor LED's. In the embodiment of the flexible tracking device 140 shown in FIG. 4, the flexible tracking device 140 is attached to surgical navigation system 50 directly by cable 146, which is attached to the flexible tracking device 140 by a flexible cable extension 148 of the flexible tracking device 140. Flexible cable 148 is attached to cable 146 by a coupling 150. The cable 146 includes a connection from an external power source (not shown) to each LED in the array of LED's 144 through the flexible cable extension 148. As shown in FIG. 4, the entire flexible tracking device 140 is capable of being sold as a disposable item in a pre-sterilized condition. The flexible tracking device 140 can be coupled with cable 146 at a distance from the patient 86 such that a sterile field can be maintained during a surgical procedure. As shown in FIG. 4, the flexible array 140 conforms to the features of patient 86 including the bony structures of the nose, forehead and cheekbones to provide a suitably firm surface such that the array of LED's 144 can be used for surface matching to register with previously scanned data. The detail of the electric connection 149 from the coupling 150 to the array of LED's 144 is shown in FIGS. 5 and 6.

Figure 5:
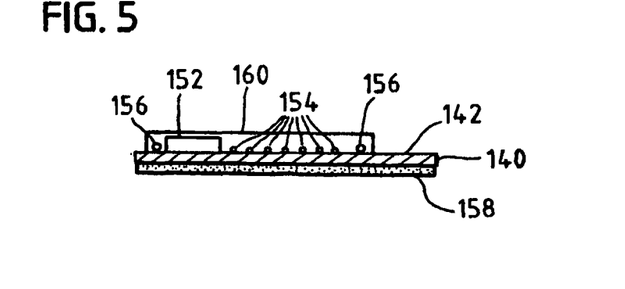
FIG. 5 is a cross section of the flexible tracking device taken generally along the lines 5-5 of FIG. 4.
Figure 6:
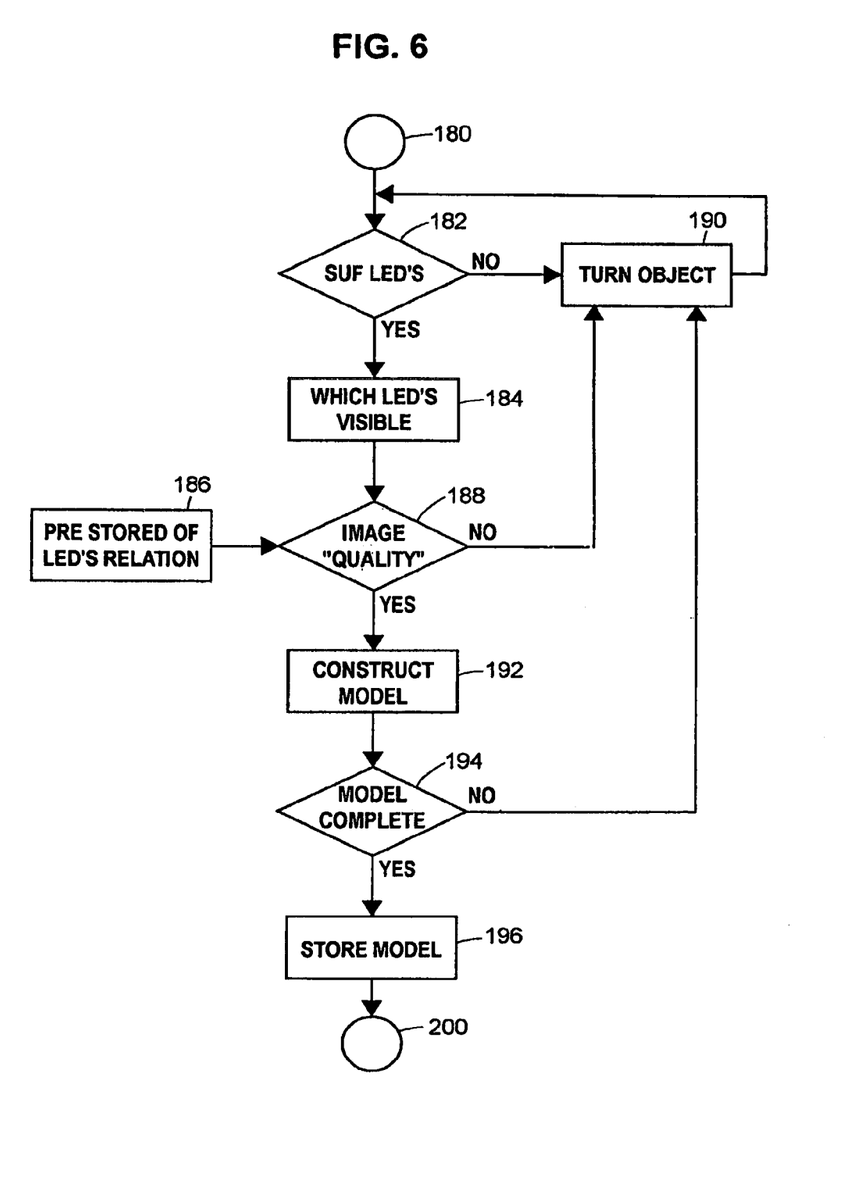
FIG. 6 is a flow diagram of a computer program for creating a model embodying one aspect of the method of the present invention.

With reference to FIG. 5, a cross sectional view of the flexible tracking device 140 is shown. As shown in FIG. 5, the electric connections 149 of the flexible tracking device 140 have a negative flexible conductive circuit 154 and a positive flexible conductive circuit 156 electrically connected to each LED 152 in the array of LED's 144. The negative flexible conductive circuits 154 are sequentially connected to the negative terminals of each LED 152. Similarly, the positive flexible conductive circuit 156 is connected to the positive terminal of each of the LED's 152. As shown in FIGS. 4 and 5, the negative flexible conductive circuits 154 and the positive flexible conductive circuit 156 can be formed directly on the surface of flexible sheet 142. The negative flexible conductive circuits 154 and the positive flexible conductive circuit 156 can formed from any suitable conductive material such as copper aluminum, silver, and the like. In addition, conductive inks can also be used to print the electric circuits 149 directly onto the flexible sheet 142. Examples of conductive ink materials include conductive copper inks, conductive silver inks and any other suitable materials that can be applied to form a flexible circuit that will transmit electricity and also can be sterilized at least one time. The electric connections 149 can be formed on the flexible substrate by any conventional method such as standard chemical etching techniques where a solid plane of copper is etched to remove the copper from the non-conducting areas to reveal the conductive traces or screen or other conventional printing processes used to print conductive circuits.

The LED 152 is bonded directly to flexible sheet 142 by soldering the LED directly to the negative flexible conductive circuits 154 and the positive flexible conductive circuit 156. In addition, the LED 152 is coated with an essentially optically transparent coating to form an essentially transparent protective coating 160. Suitable materials for this coating include transparent epoxy compounds conventionally used in the industry. Coating 160 protects the LED 152 from inadvertent movement. It is not necessary for coating 160 to completely cover the entire surface of flexible substrate 142. However, while it is not shown in FIG. 5, it may be desirable for the coating 160 also to cover the negative flexible conductive circuits 154 and the positive flexible conductive circuit 156. Typically this is not necessary because a protective coating is formed as part the normal flexible circuit manufacturing process that covers the negative flexible conductive circuits 154 and the positive flexible conductive circuit 156. The protective coating formed during the manufacturing process is removed only where connections to the LED 152 are to be made.

The flexible sheet 142 can be formed from any suitable surgically acceptable flexible insulating sheet material such as industry standard flexible FR4 sheet materials. These flexible sheet materials are available from a number of commercial sources. The base materials for most flexible FR4 sheets are polymeric materials such as polyimide, polyester, and the like.

Lastly, as shown in FIG. 5, attached to the back of flexible sheet 142 is an adhesive 158. The adhesive 158 can be any adhesive suitable for human contact. Also, it is preferable that the adhesive 158 be a contact adhesive which while reasonably tacky to a patient's skin is one that can be removed without damage to the patient's skin. Examples of suitable adhesives for use in the present invention include contact adhesives such as surgical adhesives, hairpiece adhesives or other similar adhesives that are suitable for use in contact with human skin.

As shown in FIGS. 4 and 5, the flexible circuits 154 and 156 are arranged on the flexible tracking device 140 such that the flexible tracking device 140 can be trimmed to fit a particular situation without disabling any of the LED's 152 that remain after the flexible tracking device 140 has been trimmed.

With reference to FIG. 6 that shows a flow diagram for creating a model of a surface for use in the method of the present invention. The method begins at a block 180 that initiates the formation of a model from the array of LED's on the flexible tracking device 140. Control passes to a block 182 that determines if a minimum number of LED's on the flexible tracking device 140 are visible to the camera 70. If insufficient LED's are visible, the control passes to a display block 190 that instructs the user to turn the object so more LED's will be visible. Based on the identity of the LED's that are visible, the block 190 will instruct the user as to which way to move the object. If sufficient LED's are visible, the block 182 will pass control to a block 184 that determines the identity of all visible LED's. After the identity of the visible LED's has been fully determined, a block 188 will determine the quality of the various LED's that are visible by comparing the location of the visible LED's with a database of relationships among the LED's within the array of LED's that has been stored in a block 186. The quality of the LED image relates to the direction each particular LED is pointing. If an LED points directly at the camera 70, the quality of that LED's image is considered good. However, if an LED is pointing in a direction that is not normal to the camera 70, the positional data from that LED is not as reliable. If there are insufficient LED's pointing normal to the camera 70, the block 188 will again pass control to the display block 190 that will instruct the user to move the object.

If the block 188 determines that the image quality of the visible LED's is acceptable, control passes to a block 192 that constructs a model of the shape of the object from the LED's that are visible. The model is created by determining a series of planes from groups of visible LED's. Thereafter these planes are combined to create the model of the object. The more LED's that are visible, the more precise the model will be. If a previously created preliminary model has been created, the block 192 will combine the data from the preliminary model with the new position data for the additional LED's and create a more refined model. After the model has been constructed, control passes to a block 194 that determines if all LED's have been used to construct the model created by the block 192. If less than all LED's have been used, then the block 194 will consider the model created by the block 192 as a preliminary model and control passes to the display block 190 that instructs the user to turn the object and the process is repeated until all LED's have been used to create the model. While the method has been described with a system that requires all LED's to be used to construct the model, if there are a large number of LED's on the flexible tracking device, the block 194 could be programmed to accept some number less that all LED's and consider the model complete. In this case, the system could update the model as more LED's become visible after registration as described below, in which case, the system would update the model with the newly created model created as the object is moved during a procedure. Once the block 194 determines that sufficient LED's have been used to create the model, that the model is sufficiently described and is complete. Control then will pass to a block 196 that stores the model in the memory 60 of the computer 56 for use in the registration process to be described below. Control then passes to a block 200 that begins the registration process.

Figure 7:
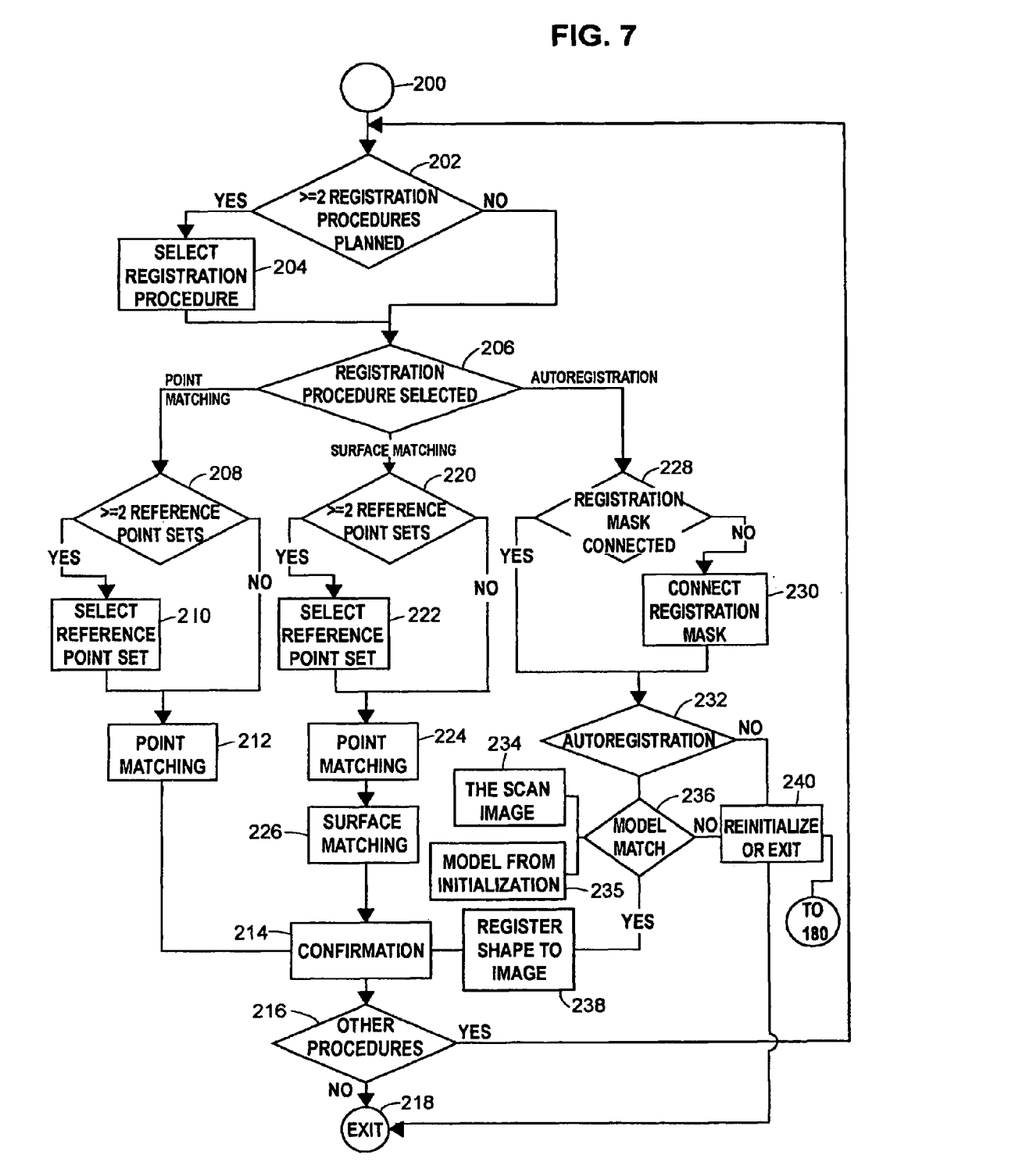
FIG. 7 is a flow diagram of computer program for registration of scan data embodying one aspect of the method of the present invention.

Turning now to FIG. 7 that shows a flow diagram of the registration process that as an aspect of the present invention. The method continues at the block 200 that initiates the registration procedure. Control passes to a block 202 that checks to see the number of registration procedures that have been planned and have not been executed. If there is only one remaining registration procedure planned, the system branches to a display and decision block 206. If there is more than one unexecuted registration procedure, control passes to a display box 204 that displays a messaged that the user must select a particular registration procedure and the system also displays the unexecuted registration procedures that have been planned so that the user can select the next procedure to execute. After the user selects the next registration procedure, the system moves to the display and decision block 206. The display and decision block 206 displays the following user selectable registration procedures: point matching, surface matching or auto registration.

If the user chooses point matching at the display and decision block 206, the system branches to a block 208 that determines how many reference sets are available. If the block 208 determines there are two or more reference sets, the system passes control to a block 210 that displays a message for the user to select a reference set. The system waits until a suitable set is selected. After one reference set is selected, the system moves to a block 212 that conducts a conventional point matching routine using well defined landmarks of the object, such as the tip of the nose or the inside of the ear. After the block 212 has conducted the point matching routine, the system moves to a block 214 that confirms success of the registration procedure. After the block 214 is executed, the system then determines by a block 216 if a further registration procedure has been planned. If the system determines there are no further registration procedures planned, the system moves to an exit block 218. However, if the system determines there are further registration procedures planned the system loops back to the block 200 and the method is again conducted until there are no further unexecuted planned registration procedures.

If the user chooses surface matching at the display and decision block 206, the system branches to a block 220 that conducts an identical determination to that conducted by the block 208 previously described. If the block 220 determines there are two or more reference sets available, the system branches to a block 222 that conducts an identical determination to that conducted by the block 210 previously described. The system then passes to a block 224 that conducts a conventional point matching procedure. After the point matching procedure is concluded, the system moves to a block 226 that conducts a conventional surface matching procedure using the information generated by the point matching procedure. After the block 226 has conducted the surface matching routine, the system moves to a block 214 that confirms success of the registration procedure. After the block 214 is executed, the system then determines by a block 216 if a further registration procedure has been planned. If the system determines there are no further registration procedures planned, the system moves to an exit block 218. However, if the system determines there are further registration procedures planned the system loops back to the block 200 and the method is again conducted until there are no further unexecuted planned registration procedures.

If the user chooses auto registration at the decision and display block 206, the system branches to a block 228 that determines if the flexible tracking device 140, or a similar device, has been connected to the system. If the flexible tracking device 140 has not been connected, the system branches to a display block 230 that instructs the user to attach the flexible tracking device 140 to the system. The system then waits until the user either attaches the appropriate flexible tracking device or the user chooses to exit the procedure. After the system determines that the flexible tracking device 88 has been attached, the system moves on to an auto registration block 232. The auto registration block 232 determines if a shape model has been constructed during the initialization procedure. If no model has been constructed, control passes to a display block 240 that instructs the user to initialize the system to create a model or exit. If a model has been constructed and has been stored in a block 235, control passes to a block 236 that determines if the shape model from the block 235 matches the scanned image from a block 234 in the memory 60 of the computer 56 within a predetermined and prestored error level. If the image and the shape model are within the error level, a block 238 registers the location of the flexible tracking device to the scanned image and the system passes control to the block 214 that confirms success of the registration procedure and proceeds as described above. If the block 236 determines the scanned image and the shape model are not within the acceptable error level, the display block 240 instructs the user to reinitialize the model creation. Alternatively, the user can choose to exit the auto registration procedure and choose a different registration method.

In addition, while the invention has been described with reference to a surgical system using scanned images of a patient, the method and flexible tracking device can be used to register the shape of any article to a scanned image, such as manufacturing work pieces, and the like.

INDUSTRIAL APPLICABILITY

The present invention is useful to quickly, easily and in a non-invasive manner enable a surgical system to track and register preoperative and intraoperative scanned images to a patient's anatomy without the need for invasive marking procedures.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A surgical navigation system comprising:
a tracking device comprising a flexible substrate and multiple tracking points disposed on the flexible substrate at intervals thereon;
a surgical tracking system that tracks the positions of the tracking points;
a data link that enables communication from the flexible substrate to the tracking system; and
a registration routine associated with the tracking system, wherein the registration routine registers the positions of the tracking points to an image of a patient, and wherein the registration routine registers the positions of each tracking point in a model with previously created scan data of the patient by determining if the locations of the tracking points in the model match the scan data of the patient within a predetermined error level.

2. The surgical navigation system of claim 1, wherein the substrate is shaped to fit the nose and forehead of the patient.

3. The surgical navigation system of claim 1, wherein the tracking points comprise optical tracking points.

4. The surgical navigation system of claim 3, wherein the tracking system comprises a computer implemented navigation system including a plurality of cameras for viewing the optical tracking points.

5. The surgical navigation system of claim 4, wherein the tracking points are disposed on a first surface of the flexible substrate, and wherein an adhesive layer is disposed on a second surface of the flexible substrate opposite the first surface to attach the substrate to a portion of the patient.

6. The surgical navigation system of claim 5, wherein the optical tracking points are light emitting diodes.

7. The surgical navigation system of claim 6, wherein the light emitting diodes are connected to a power source comprising a battery by flexible conductive circuits.

8. The surgical navigation system of claim 7, wherein each light emitting diode has its own separate conductive circuit.

9. The surgical navigation system of claim 8, wherein the conductive circuits and the tracking points are arranged such that the flexible substrate can be trimmed to fit a given surface without deactivating any tracking points that remain attached to the flexible substrate.

10. The surgical navigation system of claim 3, comprising at least ten optical tracking points.

11. The surgical navigation system of claim 10, comprising at least twenty-five optical tracking points.

12. The surgical navigation system of claim 1, wherein the data link comprises an infrared communication transceiver.

13. A tracking device comprising:
- a flexible substrate, wherein the flexible substrate has a shape that conforms to a portion of a patient;
- a plurality of tracking points on the flexible substrate spaced at intervals thereon; and
- a data link that enables communication from the flexible substrate to a surgical tracking system;
- wherein a registration routine associated with the tracking system registers the position of each tracking point in a model with previously created scan data of the patient by determining if the locations of the tracking points in the model match the scan data of the patient within a predetermined error level.

14. The tracking device of claim 13, wherein the tracking points comprise light emitting diodes.

15. The tracking device of claim 14, comprising at least ten light emitting diodes.

16. The tracking device of claim 14, wherein the surgical tracking system comprises a computer implemented navigation system including a plurality of cameras for viewing the light emitting diodes.

17. The tracking device of claim 14, wherein an adhesive layer is disposed on a side of the substrate opposite the light emitting diodes to attach the substrate to a patient.

18. The tracking device of claim 13, wherein the data link comprises an infrared communication transceiver.

* * * * *